United States Patent [19]

Kira

[11] Patent Number: 4,857,069
[45] Date of Patent: Aug. 15, 1989

[54] ARTIFICIAL VESSEL AND PROCESS FOR PREPARING THE SAME

[75] Inventor: Kazuaki Kira, Kobe, Japan

[73] Assignee: Kanegafuchi Kagaku Kogyo Kabushiki Kaisha, Osaka, Japan

[21] Appl. No.: 165,365

[22] Filed: Feb. 29, 1988

Related U.S. Application Data

[63] Continuation of Ser. No. 840,169, Mar. 17, 1986, abandoned, which is a continuation-in-part of Ser. No. 706,693, Feb. 28, 1985, abandoned.

[30] Foreign Application Priority Data

| Mar. 1, 1984 | [JP] | Japan | 59-39972 |
| Mar. 7, 1984 | [JP] | Japan | 59-44396 |
| Mar. 16, 1984 | [JP] | Japan | 59-51768 |
| Mar. 19, 1984 | [JP] | Japan | 59-52674 |
| Jan. 29, 1985 | [JP] | Japan | 60-14909 |
| Feb. 9, 1985 | [JP] | Japan | 60-23983 |

[51] Int. Cl.⁴ ............................. A61F 2/06
[52] U.S. Cl. ........................ 623/1; 128/334 R
[58] Field of Search ............ 623/1, 11, 66, 3, 12; 128/DIG. 22, 334 R

[56] References Cited

U.S. PATENT DOCUMENTS

| 3,745,203 | 7/1973 | Harper . | |
| 3,991,147 | 11/1976 | Knipp et al. . | |
| 4,173,689 | 11/1979 | Lyman et al. . | |
| 4,208,745 | 6/1980 | Okita | 623/1 |
| 4,234,535 | 11/1980 | Okita . | |
| 4,254,180 | 3/1981 | Kline . | |
| 4,286,341 | 9/1981 | Greer et al. . | |
| 4,304,010 | 12/1981 | Mano . | |
| 4,321,711 | 3/1982 | Mano . | |
| 4,355,426 | 10/1982 | MacGregor . | |
| 4,550,447 | 11/1985 | Seiler, Jr. et al. . | |
| 4,578,077 | 3/1986 | Joh | 623/3 |
| 4,604,762 | 8/1986 | Robinson . | |
| 4,610,688 | 9/1986 | Silvestrini et al. | 623/1 |
| 4,623,347 | 11/1986 | Kira | 623/1 |
| 4,655,771 | 4/1987 | Wallsten | 623/1 |
| 4,656,083 | 4/1987 | Hoffman et al. | 128/DIG. 22 X |

FOREIGN PATENT DOCUMENTS

| 2931 | 7/1979 | European Pat. Off. . | |
| 0117072 | 8/1984 | European Pat. Off. . | |
| 0130401 | 1/1985 | European Pat. Off. . | |
| 2941279 | 4/1980 | Fed. Rep. of Germany . | |
| 3204719 | 9/1982 | Fed. Rep. of Germany . | |
| 1265246 | 3/1972 | United Kingdom . | |
| 2033233 | 5/1980 | United Kingdom . | |
| 2077107 | 12/1981 | United Kingdom . | |
| 2092894 | 8/1982 | United Kingdom . | |
| 8201647 | 5/1982 | World Int. Prop. O. | 623/1 |

OTHER PUBLICATIONS

Szycher et al, Synthetic Biomedical Polymers. Concepts and Applications, 1980, pp. 29–38.

Primary Examiner—Alan W. Cannon
Attorney, Agent, or Firm—Armstrong, Nikaido, Marmelstein, Kubovcik, and Murray

[57] ABSTRACT

An artificial vessel having a compliance and a stress-strain curve approximate to those of a vital vessel, which comprises a porous part of an elastomer having pores which communicate between the inside of the vessel and the outside of the vessel and a tubular part of fibers, said tubular part being in contact with and/or bonded to at least one part of the porous part. The artificial vessel can be prevented from breakage and damage at a high blood pressure and has an excellent durability.

10 Claims, 2 Drawing Sheets

ARTIFICIAL VESSEL AND PROCESS FOR PREPARING THE SAME

CROSS-REFERENCE TO RELATED APPLICATION

This application is a continuation of application Ser. No. 840,169, filed 3/17/86, now abandoned, which is a continuation-in-part of Ser. No. 06/706,693, filed 2/28/85, now abandoned.

BACKGROUND OF THE INVENTION

The present invention relates to an artificial vessel which has a stress-strain curve and a compliance approximate to those of a vital vessel, and has pores throughout the thickness of the vessel wall, and relates to a process for preparation of the same.

In recent days, investigation on an artificial vessel has proceeded and many artificial vessels have been developed with the progress of vascular surgery. At present, examples of the clinically used artificial vessels for arteries with a large diameter of not less than 6 mm are, for instance, the DeBakey artificial vessel made of woven Dacron (USCI. Co., Ltd. of U.S.A.), and Gore-Tex (Gore. Co., Ltd. U.S.A.) which is made of an expanded potytetrafluorethylene (hereinafter refered to as "EPTFE").

Those conventional artificial vessels have pores which communicate between the inside of the vessel and the outside the vessel. When the vessel is grafted into a living body, the outside of the vessel is covered with pseudointima and the pseudointima grows into the communicating pores to cover the inside of the vessel, i.e., the vessel is organized, which prevents the formation of thrombus or occlusion by thrombus and thus makes the artificial vessel stable in the living body. The property whereby the communicating pores serve to make the artificial vessel organize is referred to as "porosity".

The compliances of such conventional artificial vessels are very different from those of vital vessels, which causes various problems due to compliance mismatch such as anastomotic punnus hyperplasia long after the grafting in a living body. Particularly, the conventional artificial vessels cannot be clinically used as an artificial artery with a small diameter of not more than 6 mm because the compliance mismatch remarkably increases to make patency of the vessel poor. Therefore self-veins are used for vascular reconstructive surgery of coronary arteries or arteries below the knees.

For the above reason, in development of artificial vessels, particularly artificial arteries with a small diameter, it is important that the compliances of artificial vessels are matched with those of vital vessels, in addition the artificial vessels having a porosity and the blood compatibility of artificial vessels being improved.

According to the report by Sasajima et al, J. Artif. Organs 12(1), 179-182(1983), however, the compliance of the practically available artificial vessels is much smaller than those of vital vessels, as shown in Table 1. As is clear from Table 1, the practically available artificial vessels are very hard to comparison with vital arteries, in other words, the artificial vessel is like a rigid vessel.

TABLE 1

| Vessel | Compliance |
| --- | --- |
| Thoracic aorta of dog | 0.749 |
| Abdominal aorta of dog | 0.491 |
| Carotid artery of dog | 0.356 |
| Double Velour Dacron | 0.058 |
| Woven Dacron | 0.021 |
| EPTFE | 0.028 |

In order to solve such compliance mismatch, a process for preparing an artificial vessel of an elastomer which has a porous wall and a compliance approximate to that of a vital vessel is disclosed in U.S. Pat. No. 4,173,689. The artificial vessel prepared according to the process does not have porosity. Further, the artificial vessel has very small pores on its wall and a relatively dense structure. Although the compliance of the artificial vessel prepared according to the process disclosed in the U.S. Patent is surely larger than that of the conventional artificial vessel, the compliance is still smaller than that of a vital vessel and is not sufficient.

For preparing an artificial vessel approximate to a vital vessel, it should be attempted to match the stress-strain curve of an artificial vessel with that of a vital vessel. The typical stress-strain curve of one of the prior artificial vessels is curve I in FIG. 4, and stress-strain curves of vital vessels are curves III and IV in FIG. 4. As is clear from FIG. 4, when a high blood pressure beyond normal blood pressure range is applied to those vessels, the stress-strain curve I of the prior artificial vessel shows different behaviour from those of the curves III and IV of the vital vessels. Accordingly, the prior artificial vessels have possibilities of breakage and damage when an abnormal blood pressure is applied, for instance, in a surgical operation, and also have insufficient durability.

An object of the present invention is to provide an artificial vessel having a porosity, and also having a compliance and a stress-strain curve approximate to those of a vital vessel.

Another object of the invention is to provide a process for preparing such an artificial vessel.

These and other objects of the invention will become apparent from the description hereinbelow.

SUMMARY OF THE INVENTION

According to the present invention, there is provided an artificial vessel having a compliance and a stress-strain curve approximate to those of a vital vessel, which comprises a porous part of an elastomer and a tubular part of fibers which are in contact with and/or are bonded to at least one part of the porous part.

The artificial vessel can be prepared according to a process comprising a step of coating a mandrel with an elastomer solution containing a pore-forming agent and/or an elastomer solution having a cloud point, and a step of immersing the coated mandrel into a coagulating liquid, the steps being repeated one or more times, wherein a tubular element of fibers is arranged on the mandrel in at least one of the steps.

DETAILED DESCRIPTION

Figure 1A:
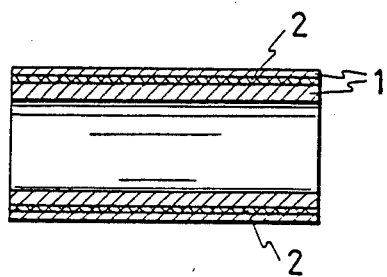
FIGS. 1A and 1B show a schematic longitudinal sectional view and a schematic cross sectional view respectively of an embodiment according to the present invention.

The elastomer used in the present invention is a thermoplastic elastomer which has fine blood compatibility. Namely the elastomer does not release any low molecular compound which causes acute poisoning, inflammation hemolysis, fever, and the like, and does not subject the blood to serious damage. The thermoplastic elastomer also has a superior antithrombogenicity. Examples of the elastomers are, for instance, polystyrene elastomers, polyurethane elastomers polyolefin elastomers, polyester elastomers, elastomers which are blended with other polymers to the extent of retaining the property of an elastomer, and a mixture thereof. Among them, a hydrophobic elastomer having a critical suface tension of less than 35 dye/cm, preferably less than 30 dyn/cm is suitably employed.

When the hydrophobic property of the elastomer becomes larger, the artificial vessel has advantages in that affinity of the grafted artificial vessel to soft tissues surrounding the vessel can be reduced, that interaction between the artiticial vessel and blood components can also be reduced and that water resistance of the artificial vessel becomes large. It should be noted that, when the affinity is large, there is a tendency that soft tissues are formed thickly around the grafted artificial vessel and are tightly fixed to the vessel. This results in the artificial vessel becoming narrower and deformed.

From viewpoints of strength, elongation, durability and antithrombogenicity, polyether type segmented polyurethane elastomers are more preferable. A segmented polyurethane which contains fluorine atom in a hard segment or a soft segment, and a segmented polyurethane disclosed in Japanese Unexamined Patent Publication (KOKAI) No. 211358/1982, which contains dimethylsiloxane in its main chain, are still more preferable. Particularly preferable is a segmented polyurethane which contains, in a part of a soft segment, dimethylsiloxane having the formula:

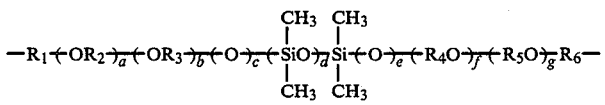

wherein $R_1$, $R_2$, $R_3$, $R_4$, $R_5$ and $R_6$ are an alkylene group having at least 1 cabon atom, preferably an alkylene group having 2 to 6 carbon atoms such as ethylene, propylene, butylene or hexamethylene; a and g are 0 or an integer of 1 to 30; b, c, e and f are 0 or 1; d is an integer of not less than 2.

In the artificial vessel of the present invention, the wall of the vessel comprises the porous part of the elastomer and the tubular part of fibers.

According to the present invention, the porous part exists over the entire thickness of the vessel wall from the inner surface to the outer surface. The pores are communicated with each other in at least one part thereof, and open to the exterior on the inner surface and the outer surface of the vessel. Therefore, the artificial vessel has porosity. The pores are defined by continuous partitions of the elastomer. It is preferable, for obtaining the artificial vessel having a compliance and a stess-strain curve approximate to a vital vessel, that the partition has a number of small pores and holes with a maximum diameter of less than 1 $\mu$m, which makes the partition bulky. Such a bulk structure cannot be formed by drying a coated elastomer solution or by cooling a molten elastomer, but can be readily formed according to the process of the present invention. The most preferable porous structure is a network structure where substantially uniform pores are formed over the entire thickness of the vessel wall from the inner surface to the outer surface.

The porous parts in the inner surface area and the outer surface area are sometimes relatively dense in comparison with the predominant part between the two areas. In such a case, the pore does not have a completely even diameter throughout its length. Unless the unevenness of diameter has a bad influence on the porosity, however, the pore having such an uneven diameter is regarded as a uniform pore. The maximum diameter of the pore is preferably 1 to 100 $\mu$m, more preferably 3 to 75 $\mu$m. When the maximum diameter is larger than 100 $\mu$m, the strength of the vessel tends to be weak and its porosity tends to be too big. When the maximum diameter is smaller than 1 $\mu$m, the porosity of the vessel tends to be small and the compliance of the vessel also tends to be too small.

There are openings formed by the pores of the porous structure in the inner and outer surfaces. Although the shape of the small pores are not particularly limited, it is preferable that the opening in the inner surface is a circle or oval. The maximum diameter of the opening is 1 to 100 $\mu$m, more preferably 5 to 50 $\mu$m, most preferably 10 to 30 $\mu$m. When the maximum diameter is larger than 100 $\mu$m, the flow of blood is disturbed and the antithrombogenicity is reduced. When the maximum diameter is smaller than 1 $\mu$m, it takes a long time to organize the artificial vessel.

The compliance of the porous part is approximate to that of a vital vessel or may be larger than that of a vital vessel. When the compliance of the porous part is larger than that of a vital vessel, the total compliance of the artificial vessel can be adjusted by combination of the tubular element of fibers. The porous part of the vessel having such a compliance can be prepared by controlling the percentage of the pores in the porous part, strength of the partition, strength of the elastomer, and the like.

The fiber which forms the tubular part is a fine and long fiber having a length more than 100 times larger than the diameter, which is usually employed for producing a yarn, a net yarn, a rope, a woven fabric, a knitting fabric, a braid, a nonwoven fabric, or the like. The fiber may be made of an organic material or of an inorganic material, as long as the fiber does not have any bad influence on a living body, degradation of the fiber in a living body can be negligible, and the fiber is stable in sterilizing treatment, and also the fibers can form a tubular element. From viewpoints of processability, commercial availability, pliability and uniformity, there are preferably employed a regenerated man-made fiber, a semi-synthetic fiber and a synthetic fiber. Examples of the fiber are, for instance, cellulose type fibers, protein type fibers, polyurethane type fibers, polyethylene type fibers, polystyrene type fibers, polyvinylchloride type fibers, polyvinylidene chloride type fibers, polyfluoroethylene type fibers, polyacrylic type fibers, polyvinyl alcohol type fibers, and the like. Among them, a fiber having a stretching property is more preferably employed. Examples of such a stretch fiber are, for instance, fiber having a self-stretching property such as rubber type fibers, polyurethane type fibers or polyester elastic type fibers; stretch bulked fibers such as Woolie nylon or Woolie tetron; covered yarns prepared by winding a spun yarn or filament on an elongated rubber filament or a Spandex filament; and the like.

The tubular element used in the present invention comprises the above-mentioned fiber; a yarn spun from at least one of the above-mentioned fibers; a multifilament of at least one of the above-mentioned fibers; a woven fabric, a knitting, a braid, a nonwoven fabric or a fabric combined thereof, which are produced from the above fiber, yarn or multifiber; a polyurethane foam of sponge like structure; and the like.

The tubular part may be formed by using a preformed tubular element of the fibers or by combining the fibers with the porous part of the elastomer so as to form the tubular structure at the finishing. From viewpoints of processability, workability and establishment of the stress-strain curve approximate to a vital vessel, there is preferably employed a tubular element of the knitting fabric, more preferably a tubular element of a knitting fabric of stretch yarns.

The tubular element used in the present invention is not particularly limited to the above-mentioned materials insofar as that the aritificial vessel prepared by combining the tubular element with the porous part of the elastomer has a compliance and a stress-strain curve approximate to those of a vital vessel. Such properties of the tubular part can be achieved by controlling the number of the connecting or contacting points of the fibers or yarns, by adjusting the tightness of the connecting point of the fibers or yarns, or by using a stretch fiber.

Figure 1B:
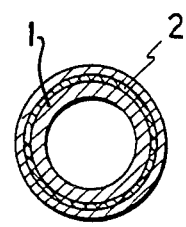
Figure 2A:
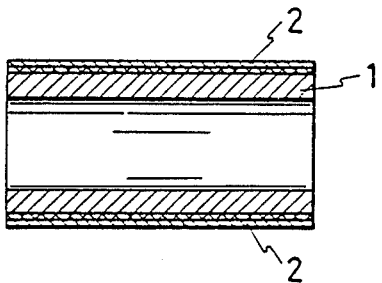
FIGS. 2A and 2B show a schematic longitudinal sectional view and a schematic cross sectional view respectively of another embodiment according to the present invention.
Figure 2B:
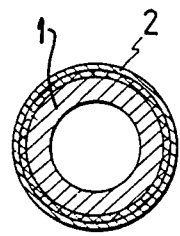
Figure 3A:
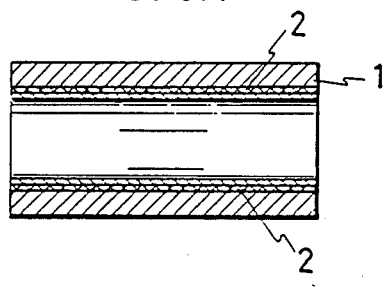
FIGS. 3A and 3B show a schematic longitudinal sectional view and a schematic cross sectional view respectively of still another embodiment according to the present invention.
Figure 3B:
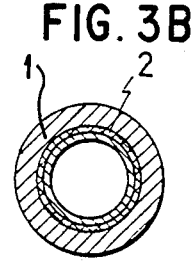

According to the present invention, the arrangement of the tubular part is not particularly limited insofar as that the tubular part is contacted with and/or bonded to at least one portion of the porous part. FIG. 1 shows an embodiment of the arrangement according to the present invention. In this embodiment, the tubular part 2 is incorporated at a middle portion of the porous part 1. In such a case there are advantages that frying of the fiber can be prevented and that a superior antithrombogenicity of the vessel can be maintained at a contact surface with blood. The tubular part 2 may be arranged at the outer side of the porous part 1, as shown in FIG. 2, so that the outer area of the tubular part 2 is exposed to the exterior of the porous part 1. Further, as shown in FIG. 3, the tubular part 2 may be arranged at the inner side of the porous part 1 so that the inner area of the tubular part 2 is exposed to the interior of the porous part 1.

The wording "the tubular part is in contact with and/or is bonded to the porous part" used herein means that there is a dynamic interaction between the tubular part and the porous part so that both the tubular part and the porous part show almost the same strain against a stress such as a blood pressure or a pressure applied from outside.

Preferable compliance for an artificial vessel cannot absolutely defined because the compliance is different depending on the diameter of the vessel, the portion to be grafted, the kind of the vessel, and the like. According to the present invention, the artificial vessel having a compliance approximate to that of a vital vessel can be produced. In general, since a compliance of a vital vessel which is used for vascular reconstruction surgery is about 0.1 to 0.8, the compliance is preferably within the range as mentioned above. According to the present invention the artificial vessel having any compliance within the range of 0.1 to 0.8 can be produced. The artificial vessel with a compliance of 0.1 to 0.8 can be preferably used as an artery with a proper diameter. Particularly the artificial vessel having an inside diameter of 1 to 6 mm with a compliance of 0.1 to 0.5 can be preferably used as an artery with a small diameter.

The "compliance approximate to that of a vital vessel" is referred to herein in the sense that the artificial vessel has the compliance approximate to that of a vital vessel having the inner diameter and the thickness of the vessel wall both approximate to those of the artificial vessel. Therefore, the artificial vessel having the inner diameter of from 2 to 6 mm, the thickness of the vessel wall of from 0.2 to 1.5 mm and the compliance of from 0.2 to 0.5 can preferably be used as arteries with a small diameter and the artificial vessel having the inner diameter of from 2 to 6 mm, the thickness of the vessel wall of from 0.4 to 1.3 mm and the compliance of from 0.3 to 0.5 can more preferably be used as arteries with a small diameter.

The "compliance" as used herein is defined by the equation (1):

$$C = \frac{\Delta V}{V_0 \cdot \Delta P} \times 100 \qquad (1)$$

wherein C is compliance, Vo is volume of a measured vessel at the inner pressure of 50 mmHg, $\Delta P$ is the pressure difference (100 mmHg) in the inner pressure of 50 mmHg to 150 mmHg, $\Delta V$ is the increase in the volume of the vessel when the inner pressure rises from 50 mmHg to 150 mmHg. In practical measurement, a vessel is inserted into a closed circuit, and the volume of an injected liquid and the pressure variation in the circuit are measured by means of a microanalysis pump and a pressure gauge. From the results, the compliance can be calculated according to the equation (1).

Figure 4:
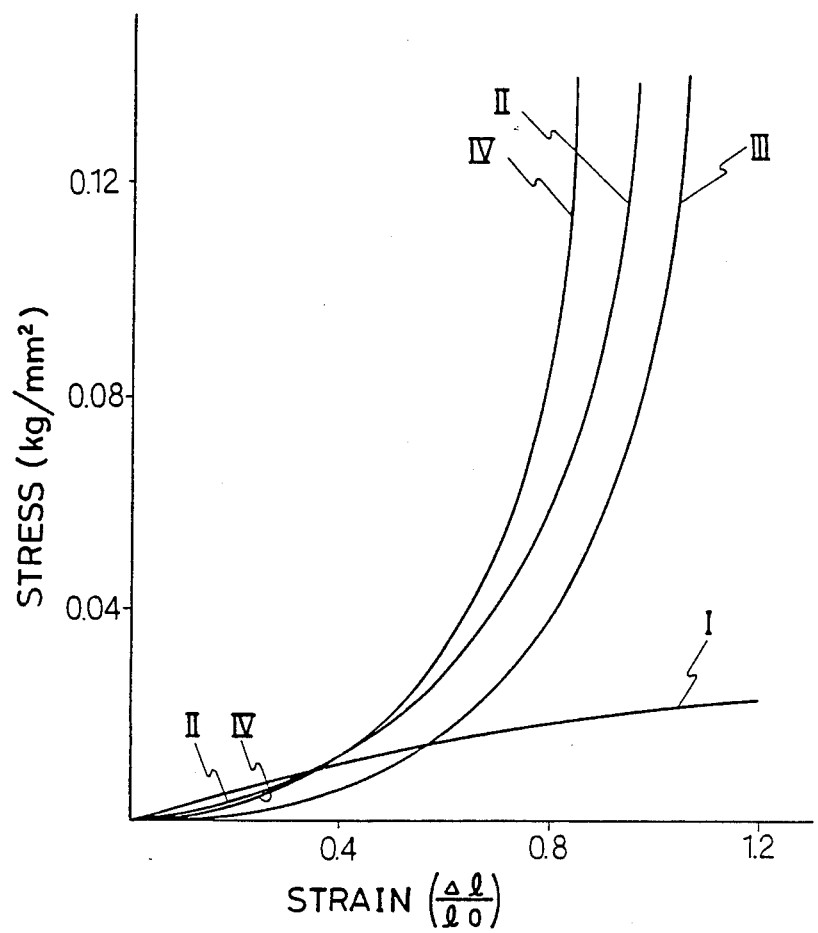
FIG. 4 is a graph of stress-stain curves of a prior artificial vessel I, an artificial vessel II of the present invention and vital vessels III, IV.

The stress-strain curves of artificial vessels and vital vessels are shown in FIG. 4. The stress-strain curves are the curves obtained by measuring in the axial direction with a tension testing machine which is usually employed in the polymer material field, for instance, Autograph IS2000 commercially available from Shimadzu Corporation.

In FIG. 4, the curve I, II, III and IV show stress-strain curves of a prior artificial vessel consisting of a porous wall made of an elastomer, the artificial vessel of the present invention, a thoracic aorta of a vital vessel and a carotid artery of a vital vessel, respectively. It is difficult to quantitatively determine a stress-strain curve of a vital vessel because the curve varies depending on the kinds of vessel such as an artery or a vein, diameter, age, individual difference, and the like. In general, however, the stress-strain curve of the vital vessels III and IV behave in common so as to show a small elastic modulus within a normal blood pressure range and to show a drastic increase of the elastic modulus when a stress beyond the normal blood pressure range is applied, as shown in FIG. 4. As is clear from FIG. 4, the artificial vessel of the present invention shows the stress-strain curve II approximate to those of the vital vessels III and IV.

The wording "a stress-strain curve approximate to that of a vital vessel" used herein means a stress-strain curve approximate to the curves III or IV.

Namely, a preferable artificial vessel of the present invention has a strain of 0.1 to 0.8, preferably 0.2 to 0.6 at a stress of 0.01 kg/mm$^2$, at which point the vessel has an elastic modulus of not more than 0.1 kg/mm$^2$, preferably 0.07 kg/mm$^2$. Also, at a stress of 0.05 kg/mm$^2$, the vessel has a strain which is larger than the strain at the stress of 0.01 kg/mm$^2$ and is of 0.4 to 1.2, preferably 0.5 to 1.0, at which point the vessel has an elastic modulus of not less than 0.12 kg/mm$^2$, preferably 0.2 to 10 kg/mm$^2$. Further, at a stress of 0.12 kg/mm$^2$, the vessel has a strain which is larger than the strain at the stress of 0.05 kg/mm$^2$ and is of 0.5 to 1.5, preferably 0.55 to 1.2, at which point the vessel has an elastic modulus which is larger than the elastic modulus at the stress of 0.05 kg/mm$^2$ and is of not less than 0.2 kg/mm$^2$, preferably not less than 0.3 kg/mm$^2$.

As a test piece for measurement of the stress-strain curve, there is preferably employed an artificial vessel as it is, because a strip prepared by cutting a vessel along its length often shows a different stress-strain curve due to change of the strength of the tubular part of the fibers. A stress-strain curve in the circumferential direction is not particularly limited, but is preferably approximate to that in the axial direction.

The "stress" is calculated by dividing the load applied at the tension test by a section area of the test piece (section area of a vessel wall) before the test. The "strain" is calculated by dividing the elongation at the test by the length of the test piece before applying the load. The "elastic modulus" is the inclination of a tangent at any point on a stress-strain curve, i.e. tangent elastic modulus.

Since the region where a small stress is applied corresponds to the region of normal blood pressure where a compliance is measured, if a compliance of an artificial vesel is approximate to that of a vital vessel, the stress-strain curve of the artificial vessl is approximate to that of a vital vessel. In the region where a large stress is applied, the stress-strain curve of the artificial vessel is approximate to that of a vital vessel to such an extent that the artificial vessel retains durability for a long time and has strength enough to prevent the vessel from breakage and damage when an abnormal blood pressure is applied to the vessel, for instance, in surgical operation.

In the artificial vessel of the present invention, the compliance and the strain measured under normal blood pressure mainly depend on the strength of the porous part made of the elastomer. The strain under a large stress beyond the normal blood pressure range depends on the strength of the tubular part made of the fibers. Accordingly, the compliance and the stress-strain curve of the artificial vessel can be made approximate to those of a vital vessel by combination of the above strengths.

According to the present invention, since the artificial vessel has the stress-strain curve approximate to that of a vital vessel, breakage and damage can be prevented when a drastic increase of blood pressure happens in surgical operation and excellent durability can be retained for a long time after grafting.

The inner surface area of the artificial vessel, that is, a surface area contacting with blood has a superior blood compatibility because the blood compatibility of the elastomer is excellent. In order to improve anti-thrombogenicity of the vessel in the first stage of grafting in a living body, the inside wall may be coated with albumin, gelatin, chondroitin sulfuric acid, a heparinized material, and the like.

The preparation of the artificial vessel of the present invention is explained hereinbelow.

The artificial vessel of the invention can be prepared in accordance with a process comprising a step for coating a mandrel with an elastomer solution containing a pore-forming agent and/or an elastomer solution having a cloud point and a step for immersing the coated mandrel into a coagulating liquid, the steps being repeated one or more times, wherein a tubular element of fibers is arranged on the mandrel in at least one of the steps.

The elastomer solution which can be used in the present invention is roughly classified into (1) an elastomer solution containing a pore-forming agent, (2) an elastomer solution having a cloud point and (3) an elastomer solution containing a pore-forming agent and having a cloud point.

The elastomer solution (1) essentially comprises a pore-forming agent, the elastomer and a solvent which can dissolve the elastomer (hereinafter referred to as "good solvent") in which the pore-forming agent are uniformly dispersed. When the elastomer solution is dipped into the coagulating liquid, the elastomer is deposited due to replacement of the good solvent with the coagulating liquid. The pore-forming agent in the deposited elastomer is dissolved and removed to give the artificial vessel of the present invention. If necessary for controlling the coagulation rate of the elastomer solution and the density or shape of the porous structure, a solvent which cannot dissolve the elastomer but can be miscible with the good solvent (hereinafter referred to as "poor solvent") may be added.

The elastomer solution (2) essentially comprises the elastomer, the good solvent and the poor solvent. The poor solvent is employed in such an amount that the solution has a cloud point. The "cloud point" means a temperature at which a dissolved polymer in a solution is deposited in a form of colloid, in other word, a temperature at which phase change occurs. When the elastomer solution (2) is handled at a temperature below the cloud point, it is difficult to form a uniform coating of the elastomer solution, and thus a proper porous structure cannot be obtained. Therefore, it is preferable to coat the mandrel with the elastomer solution at a temperature above the cloud point, and then to immerse the coated elastomer solution into the coagulating liquid of a temperature below the cloud point. According to the procedure, the porous part can be formed by changing the phase of the elastomer solution in the coating layer and depositing the elastomer in the coagulating liquid in the above order or at the same time.

The elastomer solution (3) essentially comprises the elastomer, the pore-forming agent, the good solvent and the poor solvent, the amount of the poor solvent being such an amount that the solution has a cloud point. From the elastomer solution (3), the porous part can be formed in the same procedure as in the elastomer solution (2).

The concentration of the elastomer in the elastomer solution varies depending on the kinds of elastomer or compositions of the solution, and is not particulary limited. Preferable concentration is 5 to 35% (% by weight, hereinafter the same), more preferably 10 to 30%, most preferably 12.5 to 25%. When the concentration is less than 5%, it is difficult to form a uniform porous structure. On the other hand, when the concentration is more than 35%, the elastomer solution tends to be hardly applied because of high viscosity of the solution.

The pore-forming agent is not particularly restricted insofar as it is insoluble in the good solvent and can be removed during or after the preparation of the artificial vessel. Since the artificial vessel is grafted in a living body, it is desired that the pore-forming agent is pharmacologically acceptable. Examples of the pore-forming agents are, for instance, an inorganic salt such as a common salt or calcium carbonate, a water soluble saccharose such as glucose or starch, a protein, and the like. The inorganic salt such as a common salt and the water-soluble saccharose should be treated carefully because the finely divided salt and saccharose may form a second agglomeration by moisture in the air due to their hygroscopy. From such a point of view, the protein is preferable, because even when the protein is finely divided, the fine particles do not form the second agglomeration by moisture in the air, and thus can stably produce the pores.

In addition since the protein can be easily dissolved in an alkali solution, an acid solution and a solution of an enzyme, the removal of the protein can be easily carried out. Examples of the proteins are, for instance, casein, collagen, gelatin, albumin, and the like. The particle size of the pore-forming agent is preferably not more than 74 $\mu$m, more preferably not more than 50 $\mu$m, most preferably not more than 30 $\mu$m. The "particle size" used herein means the length of a side of a sieve to be used. A pore-forming agent having a particle size larger than 74 $\mu$m tends to produce pores which are too large.

The amount of the pore-forming agent (percentage of volume of the pore-forming agent to volume of the elastomer in the elastomer solution) varies depending on the required porosity and the particle size of the pore-forming agent and the composition of the elastomer solution, particularly existence of the cloud point. The preferable amount is 20 to 500%, more preferably 50 to 350%, most preferably 100 to 300%. When the amount of the pore-forming agent is more than 500%, the porosity tends to be too large, and the viscosity of the elastomer solution tends to be too high. On the other hand, when the amount is less than 20%, the porosity tends to be poor.

Examples of the good solvent used in the present invention are, for instance, N,N-dimethylacetamide, N,N-dimethylformamide, N-methyl-2-pyrrolidone, dioxiane, tetrahydrofuran, a mixture thereof, and the like. However, the good solvent should be selected according to the kind of the elastomer used.

As the poor solvent, there can be employed any solvent which cannot dissolve the elastomer, but can be miscible with the good solvent. Examples of the poor solvents are, for instance, water, a lower alcohol, ethylene glycol, propylene glycol, 1,4-butane diol, glycerine, a mixture thereof, and the like.

The coagulating liquid may be substantially the same as the poor solvent. Examples of the coagulating liquid are, for instance, water, a lower alcohol, ethylene glycol, propylene glycol, 1,4-butane diol, glycerin, a mixture thereof, and the like. Preferable coagulating liquid is water, ethylene glycol, propylene glycol, and a poor solvent mainly comprising one of them. Most preferable coagulating liquid is a mixed solvent comprising 99 to 50% by volume of the poor solvent and 1 to 50% by volume of the good solvent. When using a mixed solvent, the excellent porosity can be easily obtained because the coagulation rate of the elastomer solution in the coagulating liquid becomes low due to the good solvent mixed with the poor solvent.

The mandrel used in the present invention is not particularly limited insofar as the mandrel is not dissolved in the elastomer solution. Preferable mandrel is a rod having a smooth surface such as a glass rod, a teflon rod or a stainless steel rod. When using dies having shapes instead of the rod, various medical articles other than the above tubular article can be obtained. For instance, if a plate is used as the die, there can be provided a film-like article which can be utilized as an artificial skin.

As typical procedure for arranging the tubular element of the fibers on or over the mandrel, there can be employed a procedure where the mandrel is covered with the tubular element, or a procedure where the fibers or a strip of the fibers are wound on the mandrel. The tubular element may be arranged directly on the mandrel or may be arranged on the mandrel via the deposited elastomer layer. It is preferable that the tubular element is arranged on the mandrel via the deposited elastomer layer and then the step for coating of the elastomer solution and the step for deposition of the elastomer are repeated one or more times.

The artificial vessel of the present invention has the following excellent properties.

(1) The artificial vessel has a porosity useful for organization of the vessel.
(2) The artificial vessel has a compliance approximate to that of a vital vessel.
(3) The artificial vessel has a stress-strain curve approximate to that of a vital vessel.

In addition, the artificial vessel of the present invention has the following usable properties, since the wall of the artificial vessel substantially comprises the porous part of the continuous elastomer and/or is bonded to the porous part.

(4) A surgical needle easily penetrates the artificial vessel, and thus the vessel is easily sutured.
(5) A bore formed by a needle can close by itself.
(6) Kinks are not formed in the practical use where blood pressure is applied.

The artificial vessel having the above-mentioned characteristic properties is excellent in patency when grafted in a living body and does not cause a problem such as anastomotic punnus hyperplasia. Also since breakage and damage of the vessel seldom happen even if blood pressure drastically increases in surgical operation, the artificial vessel can maintain durability for a long time. Further, workability of the artificial vessel in vascular reconstructive surgery is also excellent.

Therefore, the artificial vessel of the present invention can be used as an artificial vessel, an artificial vessel for by-pass, a material for patch in vascular reconstruction surgery of vital vessel, moreover, a blood access. In addition, the artificial vessel with a compliance of 0.1 to 0.8 can be used as an artificial artery. Since the artificial vessel of the present invention has the compliance and the stress-strain curve approximate to those of a vital vessel, the artificial vessel can be used as an artificial artery with a small diameter of about 1 to 6 mm whose compliance is 0.1 to 0.5, which artificial vessel has not hitherto been available in clinical use. Such artificial vessel is preferably used as an artificial vessel in vascular reconstruction surgery of arteries below the knees and as an artificial vessel for a by-pass between the aorta and coronary. In addition, the artificial vessel of the present invention can also be used as an artificial tube for a soft vital tube such as an ureter.

The present invention is more particularly described and explained by means of the following Examples. It is to be understood that the present invention is not limited to the Examples and various changes and modifications may be made in the invention without departing from the spirit and scope thereof.

EXAMPLE 1

After synthesizing a pre-polymer with 27.35 parts (part by weight, hereinafter the same) of 4,4'-diphenylmethane diisocyanate and 54.7 parts of polyoxytetramethylene glycol (average molecular weight: 2000), the pre-polymer chain was extended with 4.75 part of ethylene glycol and 13.2 parts of polydimethylsiloxane having polyethylene glycol at the both ends (average molecular weight of polyethylene glycol: 681, average molecular weight of polydimethylsiloxane: 1040) to give segmented polyurethane containing polydimethylsiloxane in the main chain.

The polyurethane thus obtained had a tensile strength of 350 kg/cm$^2$, an elongation of 670% and a critical surface tension calculated from Zisman plot of 28 dyn/cm.

In a mixed solvent of 50 ml of dioxane and 30 ml of N,N-dimethylacetamide was dispersed 22.5 g of casein having a particle size of not more than 30 $\mu$m with a homogenizer, and 15 g of the segmented polyurethane was added to the dispersion, and then was dissolved with agitation. A glass rod having a diameter of 3 mm was coated with the solution by immersing the glass rod into the solution and taking out of the solution. Subsequently, the coated glass rod was immersed into ethylene glycol to deposit the elastomer on the rod.

A tubular element having an inner diameter of about 3 mm was prepared by knitting a covered yarn with a ribbon knitting machine having a 12 needle head. The covered yarn was formed by winding a nylon fiber of 70 deniers on a Spandex of 20 deniers. After the glass rod coated with the elastomer was covered with the tubular element, the glass rod was immersed into the elastomer solution. The coated glass rod was then immersed into the coagulating liquid to deposit the elastomer in and on the tubular element, followed by removing the coagulating liquid from the surface. The coating procedure and the coagulation procedure were repeated once. After washing the deposited elastomer with water, the tubular article was taken off the glass rod. The casein particles were removed from the tubular article by dissolving in an aqueous sodium hydroxide solution of pH 13.5, and then the tubular article was sufficiently washed with water to give the artificial vessel of the present invention.

The artificial vessel obtained had an inner diameter of about 3 mm and an outer diameter of about 4.5 mm. As a result to of observation with a scanning type electron microscope, there were circular and oval openings of about 20 to 30 $\mu$m in diameter on the inner surface of the vessel, and there were circular and amorphous openings of about 1 to 10 $\mu$m in diameter on the outer surface. The tubular element was incorporated in the center part of the vessel wall and the other part was made of the elastomer of network structure which was constructed by the partitions of the elastomer and the pores, the maximum diameter of the pores being about 5 to 70 $\mu$m. The partitions had very small pores and holes with a maximum diameter of less than 1 $\mu$m which were formed by replacement between the good solvent and the coagulating liquid and thus had a bulky structure.

The porosity of the artificial vessel was confirmed by passing water through the vessel under a pressure of 120 mmHg (gauge). A volume of water which penetrating from inside to outside was about 50 ml/min per 1 cm$^2$ of the inner surface.

After pre-clotting blood of bovine origin in the vessel and cutting the pre-clotted vessel to 8 cm, the artificial vessel was inserted into a closed circuit. The ACD blood of bovine origin was fed into the closed circuit by a quantitative pump which fed 0.05 ml per stroke, and the change of the inner pressure was measured. The compliance calculated according to the equation (1) on the basis of the numbers of strokes and the change of the inner pressure was 0.30.

By using Shimadzu Autograph IS2000, a stress-strain curve was measured. The stress-strain curve of the artificial vessel was the curve II shown in FIG. 4 which is approximate to the curves III and IV of vital vessels.

The artificial vessel of about 7 cm in length was grafted to a femoral artery of an adult mongrel dog. The grafted vessel showed a patency for more than two months.

The artificial vessel did not fray when cut at any point, and was excellent in suturing property. In addition, the bores of the surgical needle closed by themselves when the needle was removed. Further, the vessel tended not to form kinks under an inner pressure of 50 to 150 mmHg.

As a result of the above data, it is clear that the artificial vessel has excellent properties as an artificial vessel for an artery with a small diameter.

EXAMPLE 2

To a mixed solvent of 45 ml of propylene glycol, 57.8 ml of dioxane and 24.8 ml of N,N-dimethylacetamide was added 22.5 g of casein having a particle size of not more than 30 $\mu$m, and then was dispersed with a homogenizer. The polyurethane prepared in Example 1 was added to the dispersion in an amount of 22.5 g and was dissolved with heating at 80° C. The resulting elastomer solution had a cloud point of about 45° C. A glass lod having a diameter of 3 mm was immersed in the solution of 80° C. to be coated uniformly with the elastomer solution. The coated glass rod was immersed into water of 18° C. to deposit the elastomer on the rod.

A tubular element having an inner diameter of about 3 mm was prepared by very roughly knitting a twist yarn of 48 Woolie teflon fibers of 2 deniers with a ribbon knitting machine having a 12 needle head. After the glass rod coated with the elastomer was covered with the tubular element, the glass rod was immersed into the elastomer solution, and then was immersed into water. After washing with water, the tubular article thus obtained was taken off the rod. The casein particles were removed from the tubular article by dissolving in an aqueous sodium hydroxide solution of pH 13.5, and then the article was sufficiently washed with water to give the artificial vessel of the present invention (inner diameter: about 3 mm, outer diameter: about 4.5 mm). In the observation of the inner surface, outer surface and section of the vessel with a scanning type electron microscope, there were oval openings of about 15 to 20 $\mu$m in diameter on the inner surface and there were amorphous openings of about 5 $\mu$m in diameter on the outer surface. The tubular element was incorporated in the center of the vessel wall and the other part was made of the elastomer of uniform network structure. The maximum diameter of the pores observed in section of the vessel wall was about 4 to 50 $\mu$m. The partitions which form a network structure had very small pores and holes with a maximum diameter of less than 1 $\mu$m which were formed by replacement between the good solvent and the coagulating liquid and thus had a bulky structure.

The penetration volume of water and the compliance measured in the same manner as in Example 1 were about 110 ml and 0.25, respectively. According to the stress-strain curve measured in the same manner as in Example 1, the relationship among the stress, the strain and the elastic modulus of the vessel was as follows:

| Stress ($kg/mm^2$) | Strain | Elastic modulus ($kg/mm^2$) |
|---|---|---|
| 0.01 | 0.35 | 0.06 |
| 0.05 | 0.65 | 0.3 |
| 0.12 | 0.75 | 1.0 |

EXAMPLE 3

15 g Of the polyurethane prepared in Example 1 was dissolved at 70° C. with agitation in a mixed solvent of 55 ml of N,N-dimethylacetamide and 30 ml of propylene glycol. The elastomer solution had a cloud point of about 40° C.

A tubular element of about 3 mm in inner diameter was prepared in the same manner as in Example 1 except that a covered yarn formed by winding a Dacron fiber of 30 deniers on a Spandex of 20 deniers was used. After covering a glass rod of 3 mm in diameter with the tubular element, the rod was immersed into the elastomer solution to be uniformly coated with the solution, and then was taken out of the solution. After allowing the rod to stand rod in air until the coating layer whitened, the glass rod was immersed into water of 15° C. to replace the mixed solvent by water. The procedures were repeated again, and then the elastomer was sufficiently washed with water. The artificial vessel was obtained by taking off the glass rod. The artificial vessel of the present invention had an inner diameter of about 3 mm and an outer diameter of about 4.5 mm.

In the observation of the inner surface, outer surface and section of the vessel with a scanning type electron microscope, on the inner surface there were oval openings of about 10 $\mu$m in maximum diameter which were uniformly distributed, and the fibers of the tubular element were partially exposed. On the outer surface, there were openings of a smaller diameter than the inner surface. The vessel wall was constructed by the tubular part of the fibers and the porous part made of the continuous elastomer partitions which define the pores. The pores had the maximum diameter of from about 8 to about 60 $\mu$m. The partitions which form pores had very small pores and holes with a maximum diameter of less than 1 $\mu$m which were formed by replacement between the good solvent and the coagulating liquid and thus had a bulky structure.

The penetration volume of water and the compliance measured in the same manner as in Example 1 were about 20 ml and 0.35, respectively. According to the stress-strain curve measured in the same manner as in Example 1, the relationship among the stress, the strain and the elastic modulus of the vessel was as follows:

| Stress ($kg/mm^2$) | Strain | Elastic modulus ($kg/mm^2$) |
|---|---|---|
| 0.01 | 0.45 | 0.045 |
| 0.05 | 0.8 | 0.21 |
| 0.12 | 1.0 | 0.5 |

What is claimed is:

1. An artificial vessel consisting essentially of first and second groups of concentric layers, said first group consisting essentially of porous fibrous material and comprising at least one concentric layer, said second group consisting essentially of porous segmented polyurethane elastomer and comprising at least one concentric layer, wherein the innermost layer of the artificial vessel is a layer of said porous segmented polyurethane elastomer, and wherein said groups have pores which communicate the inner surface of the vessel to the outer surface of the vessel, said vessel having a compliance and a stress-strain curve approximate to the compliance and the stress strain curve of a vital vessel.

2. The artificial vessel of claim 1, wherein the compliance is 0.1 to 0.8.

3. The artificial vessel of claim 1, wherein the strain is 0.1 to 0.8 at a stress of 0.01 $kg/mm^2$, the strain is 0.4 to 1.2 at a stress of 0.05 $kg/mm^2$ and the strain is 0.5 to 1.5 at a stress of 0.12 $kg/mm^2$.

4. The artificial vessel of claim 1, wherein the segmented polyurethane elastomer contains fluorine.

5. The artificial vessel of claim 1, wherein the segmented polyurethane elastomer contains a dimethylsiloxane in its main chain.

6. The artificial vessel of claim 1, wherein said fibrous layer is formed by a knit fabric.

7. The artificial vessel of claim 1, wherein said fibrous layer is formed by a knit fabric of stretch yarns.

8. An artificial vessel consisting essentially of first and second groups of concentric layers, said first group consisting essentially of porous fibrous material and comprising at least one concentric layer, said second group consisting essentially of porous segmented polyurethane elastomer and comprising at least one concentric layer, wherein the innermost layer of the artificial vessel is a layer of said porous segmented polyurethane elastomer, and wherein said groups have pores which communicate the inner surface of the vessel to the outer surface of the vessel, said vessel having a compliance of 0.1 to 0.8, and a stress-strain curve in which the strain is 0.1 to 0.8 at a stress of 0.01 $kg/mm^2$, the strain is 0.4 to 1.2 at a stress of 0.05 $kg/mm^2$ and the strain is 0.5 to 1.5 at a stress of 0.12 $kg/mm^2$.

9. The artificial vessel of claim 8, wherein said fibrous layer is formed by a knit fabric.

10. The artificial vessel of claim 8, wherein said fibrous layer is formed by a knit fabric of stretch yarns.

* * * * *